United States Patent [19]
Abdul-Sada et al.

[11] Patent Number: 5,994,602
[45] Date of Patent: Nov. 30, 1999

[54] ALKYLATION PROCESS

[75] Inventors: Ala'a K Abdul-Sada, Hove; Martin Philip Atkins, Ashford; Brian Ellis, Lower Sunbury; Philip Kenneth Gordon Hodgson, Walton-on-Thames; Mark Louis Michael Morgan, Reading, all of United Kingdom; Kenneth Richard Seddon, Belfast, Ireland

[73] Assignee: BP Chemicals Limited, United Kingdom

[21] Appl. No.: 08/902,006

[22] PCT Filed: Feb. 9, 1995

[86] PCT No.: PCT/GB95/00254

§ 371 Date: Sep. 5, 1995

§ 102(e) Date: Sep. 5, 1995

[87] PCT Pub. No.: WO95/21806

PCT Pub. Date: Aug. 17, 1995

Related U.S. Application Data

[63] Continuation of application No. 08/513,810, filed as application No. PCT/GB95/00254, Feb. 9, 1995, abandoned.

[30] Foreign Application Priority Data

Feb. 10, 1994 [GB] United Kingdom .................. 9402569

[51] Int. Cl.$^6$ .............................. C07C 2/66; C07C 2/70; C07C 2/68
[52] U.S. Cl. ......................... 585/457; 585/456; 585/459; 585/462; 585/466
[58] Field of Search .................................. 585/446, 456, 585/457, 459, 462, 466

[56] References Cited

U.S. PATENT DOCUMENTS

| | | | |
|---|---|---|---|
| 3,666,825 | 5/1972 | Torck et al. | 585/457 |
| 5,304,615 | 4/1994 | Ambler et al. | 526/189 |

*Primary Examiner*—Glenn Caldarola
*Assistant Examiner*—Thuan D. Dang
*Attorney, Agent, or Firm*—Morgan & Finnegn, L.L.P.

[57] ABSTRACT

This invention relates to a process for the alkylation of aromatics by reacting an aromatic hydrocarbon with an olefin in the presence of an ionic liquid comprising (a) a compound of the formula $R_nMX_{3-n}$ wherein R is a C1–C6 alkyl radical, M is aluminium or gallium, X is a halogen atom and n is 0, 1 or 2 and, (b) a hydrocarbyl substituted imidazolium halide or a hydrocarbyl substituted pyridinium halide wherein at least one of the said hydrocarbyl substituents in the imidazolium halide is an alkyl group having 1–18 carbon atoms. The process allows ready separation of reaction products from the ionic liquid and improves selectivity to alkylated products.

16 Claims, No Drawings

ALKYLATION PROCESS

This application is a continuation of application Ser. No. 08/513,810, filed Sep. 5, 1995, now abandoned, which is a 371 of PCT/GB95/00254, filed on Feb. 9, 1995.

FIELD OF THE INVENTION

This invention relates to process for the alkylation of aromatic hydrocarbons using an ionic liquid as catalyst.

BACKGROUND OF THE INVENTION

Alkylation of aromatics is well known in the art and is usually carried out by the reaction of an alkyl halide with an aromatic hydrocarbon in the presence of a Lewis acid catalyst such as hydrofluoric acid, boron trifluoride, concentrated sulphuric acid, zeolites and combinations thereof. More recently, acidic catalysts such as aluminium halides and the alkyl aluminium halides have been preferred, optionally in combination with a co-catalyst such as an alkyl halide. For instance, styrene has been produced by the catalytic dehydrogenation of ethyl benzene which in turn is derived by direct alkylation of benzene with ethylene in the presence of such a catalyst. Such alkylation processes are described in detail by eg Olah, G A., ed. Friedel-Crafts and Related Reactions, Interscience Publishers, J Wiley & Sons, New York (1964) and by Streitweiser, A and Reif, L., J Am Chem Soc 82, 5003 (1960). These processes use two reactors of which one is a so-called "primary alkylator" and the other is a so-called "trans- or de-alkylator". Both reactors are constructed from acid resistant materials eg Hastalloy®B or furan-lined firebrick in a 316 SS casing. Ethylene and benzene are fed into the primary alkylator in mole ratios in the range of 0.1:0.9. A catalyst complex is formulated eg by adding aluminium powder to benzene in the presence of ethyl chloride (which combination represents the promoter and catalyst) and small quantities of polyethylbenzenes. A 'red oil' catalyst complex is thus generated which is then fed into the primary alkylator in an amount which is <1% w/w of the total reactants in the primary alkylator. The 'red oil' is fed to the primary alkylator such that it totally dissolves in the benzene/ethylene system. The resultant mixture is subjected to controlled reaction conditions such that the effluent from the primary alkylator contains a mixture of unreacted benzene, ethyl benzene (the desired product), and by-products including diethyl benzene and polyethyl benzenes. This effluent stream is combined with recycled polyethyl benzenes in the trans-alkylator. The contents of the trans-alkylator, which are liquids, reach a composition which may or may not be thermodynamically controlled depending upon catalyst activity. Invariably, the effluent from the trans-alkylator will be different in composition from the primary alkylator as it will contain less benzene and more of the desired ethyl benzene. The effluent from the trans-alkylator is washed with water and alkali, eg sodium hydroxide or ammonia to destroy the catalyst. This means that that the catalyst is irretrievably lost and cannot therefore be recycled or reused. The washed material is then distilled to produce benzene for recycle, the desired ethyl benzene, di- and tri-ethyl benzenes for recycle and the remaining heavy materials such as tetra-, penta- and hexa-ethyl benzenes and impurities are recovered and used as 'flux oil'. The ethyl benzene is recovered and kept in a suitable storage facility eg in tanks, until required for the dehydrogenation stage to produce styrene.

Such catalysts have the disadvantage that some of the acids used such as hydrofluoric acid are too strong, corrosive and volatile and therefore require a considerable degree of safety measures both for the equipment used and for the operational personnel involved; others such as concentrated sulphuric acid are relatively inactive and require high reaction volumes and expensive reconcentration equipment; and zeolites are too weak therefore requiring the use of relatively high reaction temperatures. Where aluminium halides are used, they are usually miscible with the reactant hydrocarbons and have to be destroyed to recover the desired alkylated product thereby preventing recycle of the catalyst and hence adding to the cost of the process.

Alkylation of isoparaffins by olefins has also been reported in FR-A-2626572 in the presence of a catalyst comprising ionic liquids. This document, however, does not describe the alkylation of aromatics using olefins. The process of alkylation of iso-paraffins is different from that involving the alkylation of aromatics because, surprisingly, these catalysts for the alkylation of iso-paraffins—where relatively severe reaction conditions are required to obtain the desired species with high octane rating—can also catalyse the alkylation of aromatics with the desired conversion-selectivity.

Ionic liquids are primarily mixtures of salts which melt below room temperature. Such salt mixtures include aluminium halides in combination with one or more of imidazolium halides, pyridinium halides or phosphonium halides and the latter being preferably substituted. Examples of the latter include one or more of 1-methyl-3-butyl imidazolium halides, 1-butyl pyridinium halide and tetrabutyl phosphonium halides.

It has now been found that aromatic hydrocarbons can be alkylated directly with olefins without recourse of alkyl halides as the alkylating agent whilst at the same time mitigating the problems generated by the use of strong acids, expensive equipment or inability to recycle the catalysts used as described above.

SUMMARY OF THE INVENTION

Accordingly, the present invention is a process for the alkylation of aromatics by reacting an aromatic hydrocarbon with an olefin in the presence of an ionic liquid comprising
  (a) a compound of the formula $R_nMX_{3-n}$ wherein R is a C1–C6 alkyl radical, M is aluminium or gallium, X is a halogen atom and n is 0, 1 or 2 and,
  (b) a hydrocarbyl substituted imidazolium halide, a hydrocarbyl substituted pyridinium halide or mixtures thereof
wherein at least one of the said hydrocarbyl substituents in the imidazolium halide is an alkyl group having 1–18 carbon atoms.

DESCRIPTION OF SPECIFIC EMBODIMENTS

The hydrocarbyl substituted imidazolium halide or a hydrocarbyl substituted pyridinium halide is suitably selected from 1-alkyl-3-alkyl imidazolium halides and 1-alkyl pyridinium halides. Specific examples of these compounds include the following:

1-methyl-3-ethyl imidazolium chloride,
1-ethyl-3-butyl imidazoliium chloride,
1-methyl-3-butyl imidazolium chloride,
1-methyl-3-butyl imidazolium bromide,
1-methyl-3-propyl imidazolium chloride,
1-methyl-3-hexyl imidazolium chloride,
1-methyl-3-octyl imidazolium chloride, 1-methyl-3-decyl imidazolium chloride,
1-methyl-3-dodecyl imidazolium chloride,
1-methyl-3-hexadecyl imidazolium chloride,
1-methyl-3-octadecyl imidazolium chloride,
1-methyl-3-hexyl-imidazolium chloride,
1-methyl-3-octyl-imidazolium chloride,
1-methyl-3-decyl-imidazolium chloride,
1-methyl-3-dodecyl-imidazolium chloride,
1-methyl-3-hexadecyl-imidazolium chloride,
1-methyl-3-octadecyl-imidazolium chloride,
ethyl pyridinium bromide,
ethyl pyridinium chloride,
ethylene pyridinium dibromide,
ethylene pyridinium dichloride,
butyl pyridinium chloride and
benzyl pyridinium bromide.

The imidazolium halides of the present invention can be prepared by any of the well known methods described in the art especially those described eg in FR-A-2626572. In the case of the imidazolium halides which have more than 5 carbon atoms in the alkyl substituent, the following method may be used for synthesis thereof:

For instance, a 1-alkyl-3-methyl imidazolium halide can be prepared by mixing dry 1-methylimidazole with 1-alkyl haloalkane (and optionally with a solvent such as eg acetonitrile, if a homogeneous mixture is desired) and placing them eg in a Corius tube inside a dry box. The Corius tube is then closed using a super seal in the dry box and sealed under vacuum. The two components form two layers inside the Corius tube and the resulting mixture is then heated to about 100° C. for about a week. The resultant product is then cooled to room temperature to form a viscous product which is then transferred from the dry box to a Schlenk round bottomed flask and left under vacuum for a few hours. The resultant viscous liquid is then analysed for identification and characterisation of the 1-alkyl-3-methyl imidazolium halide.

The ionic liquids of the present invention contain, in addition to the imidazolium halides and/or pyridinium halides defined above, an aluminium or gallium compound which is suitably an aluminium halide or gallium halide such a aluminium trichloride or gallium trichloride, or, an alkyl aluminium/gallium halide such an alkyl aluminium/gallium dichloride or a dialkyl aluminium/gallium halide and is preferably ethyl aluminium/gallium dichloride.

It is well understood in the art that the ratio of the components in an ionic liquid used as catalyst should be such that they remain in a liquid state under the reaction conditions. When preparing multi-component ionic liquids, the presence of the imidazolium halides having more than 5 carbon atoms in the alkyl group enables such liquids to tolerate a higher proportion of the other component(s) and still remain liquids, in some cases at room temperature, than is possible with conventional imidazolium halides.

The present invention can also be carried out by using as catalyst an ionic liquid which comprises a ternary melt of:
(a) a compound of the formula $R_nMX_{3-n}$ wherein R is a C1–C6 alkyl radical, M is aluminium or gallium, X is a halogen atom and n is 0, 1 or 2,
(b) at least one of a hydrocarbyl substituted imidazolium halide and a hydrocarbyl substituted pyridinium halide, and
(c) at least one of a hydrocarbyl substituted quaternary ammonium and a hydrocarbyl substituted phosphonium halide.

The compound (a) in the ternary melt is suitably an aluminium halide, such as aluminium trichloride, a gallium halide such as gallium trichloride, or, an alkyl aluminium/gallium halide such as an alkyl aluminium/gallium dihalide or a dialkyl aluminium/gallium halide, and is preferably ethyl aluminium/gallium dichloride.

The component (b) in the ionic liquid is a hydrocarbyl-substituted imidazolium halide or a hydrocarbyl substituted pyridinium halide. These may be suitably selected from the list described above. The component (c) in the ternary melts is a hydrocarbyl-substituted quaternary ammonium halide or a hydrocarbyl-substituted phosphonium halide. Of the substituent groups in the ammonium halides at least one substituent is an alkyl group. The other substituents may be the same or different groups selected from hydrogen, alkyl, aryl, aralkyl and alkaryl groups. Similarly, the hydrocarbyl substituted phosphonium halides contain at least one hydrocarbyl group. The other substituents may be the same or different groups selected from hydrogen, alkyl, aryl, aralkyl and alkaryl groups. Specific examples of such compounds include inter alia tetra-alkyl ammonium halides or tetra-alkyl phosphonium halides in each of which the alkyl group suitably has 1–20, preferably 1–18 and more preferably from 1–6 carbon atoms.

The relative ratios of components (a), (b) and (c) in the ternary melt is suitably that they are capable of remaining in the liquid state under the reaction conditions. Typically, the relative mole ratio of component (a) to the components [(b)+(c)] in the ternary melt ionic liquid is suitably in the range from 1:2 to 3.0 :1, preferably from 1.5:1 to 2:1. Within this range, where the ionic liquid is intended for use as a reaction medium or a solvent, the amount of the component (a) can be less than 50 mole % of the total ionic liquid. However, where the ionic liquid is intended for use as a catalyst, the amount of component (a) is preferably greater than 50 mole % of the total ionic liquid. The relative mole ratios of (b):(c) in such an ionic liquid is suitably in the range from 0.01:1 bearing in mind that within this range the ratios chosen should be such that the resultant ionic liquid is a liquid at room temperature.

The ternary melts of the present invention are suitably prepared by mixing the components in an atmosphere inert under the reaction conditions for binary mixtures as described in our published EP-A-0558187. It is preferable to purify each of the components in the melt prior to preparing the melt. Thus, aluminium trichloride can be purified by repeated sublimations until the melt at the bottom of the sublimator is clear and the aluminium trichloride takes on a lustrous, shiny appearance; the hydrocarbyl substituted imidazolium or pyridinium halides can be purified by repeated recrystallisations from solutions thereof in a suitable solvent; and the hydrocarbyl substituted quaternary ammonium or phosphonium halide can be purified by dissolving the halide in a suitable solvent such as eg ethanol and precipitation of the halide from the ethanol solution by dilution with eg diethyl ether followed by filtration and drying in an inert atmosphere.

The olefins that may be used for the alkylation reaction are suitably C2–C10 olefins, preferably the lower olefins, eg the C2–C4 olefins, particularly ethylene, propylene and the butenes.

The aromatic hydrocarbons that can be alkylated by the process of the present invention are suitably monocyclic such as eg benzene and toluene, although bi-cyclic and poly-cyclic aromatics such as naphthlenes can also be alkylated.

The mole ratio of olefin to the aromatic hydrocarbon used for the alkylation reaction is suitably in the range from 0.1 to 0.9, preferably from 0.3 to 0.7 and more preferably from 0.4 to 0.6.

The alkylation reaction is suitably carried out temperature in the range from 80 to 200° C., preferably from 100 to 170° C., and at a reaction pressure in the range from 0.5 to 3.0 MPa, preferably from 1.0 to 2.4 MPa. However, it will be known to those skilled in the art that the reactor pressure will be dependent upon the temperature due to the vapour pressure of the aromatic hydrocarbon and the desire to achieve a set olefin to aromatic hydrocarbon ratio within the ranges described.

The alkylation reaction is suitably carried out in an atmosphere inert under the reaction conditions such as eg nitrogen.

The ionic liquid catalyst is suitably used in an amount from 0.1 to 1.0% w/w, preferably from 0.2 to 0.5% w/w based on the total weight of the hydrocarbon reactants in the reaction mixture.

The ionic liquid catalyst may be supplemented by a co-catalyst such as eg an alkyl halide. The alkyl group in the alkyl halide is suitably such that it corresponds to the olefin used for alkylation of the aromatic hydrocarbon. Examples of the alkyl halides that may be used include ethyl chloride and tertiary butyl chloride.

The use of ionic liquids as alkylation catalysts have the following advantages over the conventional catalysts. They:

i. readily form a separate phase from the other components of the reaction mixture due to their polar nature, acidity and density, thereby enabling recycle of the catalyst unlike conventional catalysts which are irretrievably destroyed prior to the recovery of the alkylated product from the reaction mixture;

ii. improve the selectivity to the alkylated product and hence improve the efficiency of the alkylation process; and iii. can be readily produced with a greater degree of control during manufacture unlike the conventional catalysts which suffer from the problems of variability of composition; this in turn ensures a greater degree of control of the alkylation process and leads to a smoother and more economic operation of the liquid phase alkylation process.

ILLUSTRATIVE EXAMPLES AND COMPARATIVE TESTS

The present invention is further illustrated with reference to the following Examples and comparative tests. In the Examples relating to the preparation of the uncommon alkyl imidazolium halides, the 1-methylimidazole used was distilled over sodium hydroxide and was always handled under a cover of nitrogen. The alkyl halides used were all dried over calcium hydride for a week and then distilled prior to use. It is not believed that any detailed analysis of these compounds is necessary in order to ascertain their structure since the reactions are stoichiometric, no gases are evolved nor any solids deposited during the reaction. However, in order to prove that this is the case, $^1$H NMR analyses has been carried out on the products from some of the Examples and on this basis a structure has been assigned for those products on which no NMR analyses have been carried out.

In Tables below, the intensity referred to is the peak height which corresponds to the number of protons in that position. In this respect the notations very strong, strong, medium and weak represent the following range of peak intensities (I/Io):

| very strong | 80–100 |
|---|---|
| strong | 60–80 |
| medium | 40–60 |
| weak | 20–40 |
| very weak | <20 |
| δ (ppm) | chemical shift in parts per million |

EXAMPLES

A. Preparation of Imidazolium halides

A1. Preparation of 1-pentyl-3-methyl Imidazolium Chloride

Dry 1-methylimidazole (9.03 g, 0.11 mol) was mixed with 1-chloropentane (10.66 g, 0.1 mol) in a Schlenk round bottomed flask. The two components formed two layers, and acetonitrile (40 ml) was added to make the mixture homogeneous. The mixture was heated under reflux, under cover of dry nitrogen, for 5 hours. The resultant solution was allowed to cool to room temperature and evaporated to dryness in vacuo. The solid so formed was redissolved in acetonitrile (20 ml) and cooled to −13° C. for 5 days. This resulted in the formation of crystals which were isolated by Schlenk filtration and dried in vacuo for 48 hours. The yield of 1-pentyl-3-methyl imidazolium chloride was 8.2 g (69.9%), had a melting point of 58.2° C., m/z of 341. An $^1$H NMR spectrum of the product of this Example A1 is shown below in Tables 1 and 2.

TABLE 1

Conventional $C_1/C_2$ Melt NMR of a Product containing 65 mole % of $AlCl_3$ (for comparison)

| δ (ppm) | Intensity (I/IO) | Type |
|---|---|---|
| 1.1 | strong | doublet |
| 3.4 | very strong | singlet |
| 3.8 | weak | triplet |
| 6.8 | weak | doublet |
| 7.85 | weak | doublet |

TABLE 2

$C_1/C_5$ Melt NMR of a Product containing 65 mole % of $AlCl_3$ (Example A1)

| δ (ppm) | Intensity (I/IO) | Type |
|---|---|---|
| 0.5 | very strong | singlet |
| 1.0 | very strong | singlet |
| 1.5 | medium | singlet |
| 3.5 | very strong | singlet |
| 3.8 | medium | singlet |
| 6.9 | medium | doublet |
| 7.9 | medium | singlet |

A2. Preparation of 1-hexyl-3-methyl Imidazolium Chloride

Dry 1-methylimidazole (9.03 g, 0.11 mol) was mixed with 1-chlorohexane (12.06 g, 0.1 mol) and placed in a Corius tube inside a dry box. The Corius tube was then closed using a super seal in the dry box and sealed under vacuum. The two components formed two layers, inside the Corius tube, and this mixture was heated at 100° C. for a week. The resulting product was allowed to cool to room temperature when it formed a viscous product. The viscous product was transferred from the dry box to a Schlenk round bottomed flask where it was left under vacuum for 4 hours to form a viscous liquid.

This liquid was not analysed by $^1$H NMR but the structure is that shown by analogy with that in Example A1 above. The product was a liquid at room temperature and the yield was 12.23 g (92.2%) with an m/z value of 369.

A3. Preparation of 1-octyl-3-methyl Imidazolium Chloride

The process of Example A2 above was repeated except that 1-chlorooctane (14.9 g, 0.1 mol) was used instead of 1-chlorohexane. The viscous liquid was not analysed by $^1$H NMR but by analogy with Example A1, the structure is that shown. The product was a liquid at room temperature, the yield was 15.8 g (96.6%) and had an m/z value of 425.

A4. Preparation of 1-nonyl-3-methyl Imidazolium Chloride

The process of Example A2 was repeated except that 1-chlorononane (16.3 g, 0.1 mol) was used instead of 1-chlorohexane. The viscous liquid product was not analysed by $^1$H NMR but was assigned the structure shown by analogy with Example A1. The product was a liquid at room temperature, the yield was 16.1 g (90.0%) and had an m/z value of 453.

A5. Preparation of 1-decyl-3-methyl Imidazolium Chloride

The process of Example A2 was repeated except that 1-chlorodecane (17.7 g, 0.1 mol) was used instead of 1-chlorohexane. The viscous liquid product was not analysed by $^1$H NMR but was assigned the structure shown by analogy with Example A1. The product was a liquid at room temperature, the yield was 18.3 g (94.2%) and had an m/z value of 481.

A6. Preparation of 1-dodecyl-3-methyl Imidazolium Chloride

The process of Example A2 was repeated except that 1-chlorododecane (20.48g 0.1 mol) was used instead of 1-chlorohexane. The product upon heating at 100° C. was waxy and was recrystallised from acetonitrile (50 ml) at −13° C. for a week in a Schlenk round bottomed flask. The crystals were isolated by Schlenk filtration and dried in vacuo for 48 hours. The $^1$H NMR analysis of the crystals is shown in Table 3 below. The crystals had a melting point of 52.5° C., the yield was 19.4 g (86.1%) and had an m/z value of 537.

TABLE 3

$C_1/C_{12}$ Melt NMR of a Product containing 40 mole % of $AlCl_3$ (Example A6)

| δ (ppm) | Intensity (I/IO) | Type |
| --- | --- | --- |
| 0.5 | weak | singlet |
| 0.9 | very strong | doublet |
| 1.5 | very weak | singlet |
| 3.5 | weak | singlet |
| 3.8 | very weak | singlet |
| 4.6 | very weak | singlet |
| 5.3 | very weak | singlet |
| 7.0 | very weak | singlet |
| 8.0 | very weak | singlet |

A7. Preparation of 1-tetradecyl-3-methyl Imidazolium Chloride

The process of Example A6 was repeated except that 1-chlorotetradecane (23.3 g 0.1 mol) was used instead of 1-chlorododecane. The crystals formed were not analysed by $^1$H NMR but were assigned the structure shown by analogy with Example A6. The crystals had a melting point of 56.89° C., the yield was 23.9 g (93.3%) and had an m/z value of 593.

A8. Preparation of 1-hexadecyl-3-methyl Imidazolium Chloride

The process of Example A6 was repeated except that 1-chlorohexadecane (26.09 g 0.1 mol) was used instead of 1-chlorododecane. The crystals were not analysed by $^1$H NMR but were assigned the structure shown by analogy with Example A6. The crystals had a melting point of 61.6° C., the yield was 25.7 g (89.6%) and had an m/z value of 649.

A9. Preparation of 1-octadecyl-3-methyl Imidazolium Chloride

The process of Example A6 was repeated except that 1-chlorooctadecane (28.9 g 0.1 mol) was used instead of 1-chlorododecane. The crystals were not analysed by $^1$H NMR but the structure was assigned on the basis of analogy with Example A6. The crystals had a melting point of 71.07° C., the yield was 31.77 g (93.3%) and had an m/z value of 705.

B. Preparation of Ternary Melt Catalysts

B1. Purification of Aluminium Trichloride

In an inert-atmosphere box, anhydrous aluminium trichloride (ca. 200 g) was placed in a sublimator with sodium chloride (2 g) and powdered aluminium (1 g). The apparatus was transferred to a vacuum line where the mixture was heated in vacuo in a silicone oil-bath, to 150° C. The aluminium trichloride was left to sublime until ca. 10% of it remained at the bottom of the sublimator together with the molten NaCl and impurities. After cooling, the apparatus was placed back into the inert-atmosphere box where the sublimed $AlCl_3$ was removed by scraping and then placed again into a clean apparatus with NaCl (2 g) for re-sublimation. (Powdered aluminium was utilized in the first sublimation only, to remove iron impurities). Five successive sublimations were carried out until the melt observed at the bottom of the sublimator was clear and the $AlCl_3$ took on a lustrous, shiny appearance.

B2. Preparation of 1-ethyl-3-methylimidazolium chloride

The preparation was carried out in a fume cupboard. The apparatus comprised a round-bottomed flask provided with an additional funnel and was adapted to be heated to elevated temperature. The apparatus was purged clean with nitrogen and the reaction was carried out under nitrogen. 1-Methylimidazole (300 ml), which had previously been distilled in vacuo over KOH, was placed in the flask under nitrogen. Acetonitrile (ca. 150 ml, distilled over $CaH_2$) was then added to the flask. The mixture was then heated slowly in small increments until the internal temperature of the flask was 68° C. and then allowed to stabilize for one day. The nitrogen purge was then replaced with a stream of ethyl chloride which was administered through a flow meter at the rate of 2 dm$^3$ ethyl chloride per hour for two days. Thereafter, the flow of ethyl chloride was reduced to 1 dm$^3$ per hour and maintained at this rate for a further three days. After this duration, a solution containing the desired product was removed from the flask whilst still hot by cannula and this solution was extracted with ethyl acetate and small white crystals of 1-ethyl-3-methylimidazolium chloride were recovered from the extract. Further purification was carried out by recrystallisation from further aliquots of ethyl ethanoate.

B3. Purification of Tetra-Ethylammonium Chloride

Tetra-ethylammonium chloride (100 g) was dissolved in ethanol (150 ml). Diethyl ether was then added to this solution until tetra-ethylamonium chloride started to precipitate. The solution was cooled to −13° C. and left at this temperature overnight. The resulting crystals were filtered under dry nitrogen and then heated in a Schlenk round bottomed flask to 100° C. under vacuum for 48 hours. The resulting solid was then transferred to a dry box ready to use.

B4. Preparation of Ternary melt

Crystalline 1-ethyl-3-methylimidazolium chloride was melted in vacuo and poured into an aluminium foil "boat" under an inert atmosphere and then allowed to soldify therein. The solid so formed was then broken into large lumps. These lumps were then reacted with lumps of tetra-ethyl ammonium chloride and aluminium trichloride in varying quantities and under conditions shown in the Table 4 below to prepare six different batches (Batch Nos. 1–6) of acidic and basic melts. Lumps were used instead of powders to prevent charring of the melt during heating.

TABLE 4

| Batch No. | [Et$_4$N]Cl (g) | [MeEtim]Cl (g) | AlCl$_3$ | Ternary Melt (g) | AlCl$_3$ (Moles) |
|---|---|---|---|---|---|
| 1 | 0.8922 (23.333%) | 0.3936 (11.66%) | 2.0 | 3.287 | 0.65 |
| 2 | 0.6958 (17.5%) | 0.5922 (17.5%) | 2.0 | 3.288 | 0.65 |
| 3 | 1.2428 (40%) | 0.5498 (20%) | 1.0 | 2.793 | 0.40 |
| 4 | 0.6214 (20%) | 1.0996 (40%) | 1.0 | 2.721 | 0.40 |
| 5 | 0.3107 (10%) | 1.3745 (50%) | 1.0 | 2.680 | 0.40 |
| 6 | 0.1553 (5%) | 1.512 (55%) | 1.0 | 2.667 | 0.40 |

[Et$_4$N] is tetra-ethylammonium chloride
[MeEtim]Cl is 1-ethyl-3-methylimidazolium chloride
Ternary Melt is [Et$_4$N]/[MeEtim]Cl/AlCl$_3$ The ternary melts were characterised using $^1$H NMR spectroscopy by placing the neat ionic liquid in a 4 mm diameter NMR tube in vacuo. No solvent was used for the analysis. The results of the analysis are tabulated in Tables 5 (standard melt) 6 and 7 (ternary melt) below:

TABLE 5

$^1$NMR of Standard Binary C$_1$/C$_2$ Melt for Comparison

| δ (ppm) | Intensity (I/IO) | Type |
|---|---|---|
| 1.0 | strong | triplet |
| 3.4 | very strong | triplet |
| 3.8 | medium | doublet |
| 6.9 | medium | doublet |
| 7.8 | medium | singlet |

C$_1$/C$_2$ Melt - Stendard melt & methyl & ethyl imidazolium chlorides

TABLE 6

$^1$NMR of Ternary Melt (65% AlCl$_3$, 23.3% [Et$_4$N]Cl & 11.7% [MeEtim]Cl)

| δ (ppm) | Intensity (I/IO) | Type |
|---|---|---|
| 0.7 | very strong | singlet |
| 1.0 | weak | singlet |
| 2.6 | very strong | singlet |
| 3.3 | medium | singlet |
| 3.7 | weak | doublet |
| 4.6 | very weak | singlet |
| 6.8 | very weak | doublet |
| 7.8 | very weak | singlet |

[Et$_4$N]Cl - tetra ethyl ammonium chloride
[MeEtim]Cl - 1-ethyl-3-methyl imidazolium chloride

TABLE 7

$^1$NMR of Ternary Melt (40% AlCl$_3$, 15% [Et$_4$N]Cl & 45% [MeEtim]Cl)

| δ (ppm) | Intensity (I/IO) | Type* |
|---|---|---|
| 1.0 | very strong | singlet |
| 2.8 | very weak | singlet |
| 3.5 | very strong | singlet |
| 3.8 | strong | singlet |
| 7.4 | medium | singlet |
| 9.2 | weak | singlet |

* - all peaks were broad peaks
[Et$_4$N]Cl- tetraethyl ammonium chloride
[MeEtim]Cl - 1-ethyl-3-methyl-imidazolium chloride

C. Alkylation Using Ionic Liquids as Catalyst

The apparatus used for this Example was a Buchi autoclave (5 litre capacity) system made from 316 stainless steel. The autoclave was fitted with a temperature control jacket containing silicone oil heat transfer liquid and, electronic temperature and pressure measurement devices. The autoclave was also fitted with magnetically driven 'U'-shaped paddle stirrer (0–2000 rpm). The autoclave was connected to pressurised ethylene and nitrogen supplies. A catalyst injection system was incorporated into the nitrogen supply to the autoclave.

The autoclave was charged with benzene (500 ml, Spectrophotometric Grade, ex Aldrich Cat. No. 15,546–8) at room temperature and was then pressurised with ethylene (ex Air Products) to 1.7 MPa. The fluids inside the autoclave were then stirred at 200 rpm. Some of the ethylene dissolved in the benzene thereby producing a pressure drop which was recorded. The autoclave was topped up with more ethylene to 1.4 MPa.

The temperature of the autoclave was then raised to 105° C. When a steady temperature and pressure were attained, an ionic liquid catalyst comprising (a) 67% w/w aluminium trichloride and 33% w/w 1-ethyl-3-methyl-imidazolium chloride (10 ml, equivalent to 13.2 g) and (b) ethyl chloride (1.0 ml) was injected into the autoclave under nitrogen. The nitrogen pressure was set to 0.01 MPa above the recorded steady state autoclave pressure.

Since the reaction was instantaneous, ethylene pressures were recorded as a function of residence time after catalyst injection. Periodically, samples of the liquid reaction mixture were removed from the autoclave and analysed by Gas Chromatography using a Phillips PU 4500 chromatograph fitted with a CPSIL 5 column to separate benzene, ethyl benzene, diethyl benzene and heavier materials. The data from the GC was computed to arrive at the conversion, selectivity and yield data as a function of residence time. The reaction was allowed to continue until equilibrium was achieved as determined by a steady yield when the reaction was considered to be complete. Upon completion, the catalyst was allowed to settle into a separate phase from the liquid reaction products. The reaction products were then analysed using standard atomic absorption techniques. The results are tabulated below.

Comparative Test (Not According to the Invention)

In a comparative test, a conventional catalyst was used instead of the ionic liquid. The conventional catalyst was manufactured by adding ethyl benzene (200 ml, ex Aldrich 29,684–8) to aluminium trichloride (20 g, 99% purity) and ethyl chloride (1.0 ml) in a pre-dried glass container. The resultant slurry was agitated by shaking and allowed to stand. A 'red oil', catalyst complex as described above was formed at the solid-liquid interface. This catalyst complex was removed and stored under nitrogen.

The alkylation apparatus and procedure used was exactly the same as that for Example B above except the catalyst used was the complex 'red oil' (10 ml) prepared as above injected together with ethyl chloride (1.0 ml). The results are tabulated in Table 8 below:

TABLE 8

| Reaction Conditions | Ionic Liquid Catalyst | Red Oil Catalyst |
|---|---|---|
| $C_2H_4$:benzene (Mol Ratio) | 0.6 | 0.6 |
| Reaction Temperature (° C.) | 110 | 110 |
| Initial Pressure (MPa) | 2.4 | 2.4 |
| Stirrer speed (rpm) | 2000 | 2000 |

The detailed conditions and product analyses are tabulated below for each of the reactions described above. In Tables 9 and 10 below, the following abbreviations have been used:

| | |
|---|---|
| Bz | Benzene |
| EtBz | Ethyl Benzene |
| DEB | Diethyl Benzene |
| Conv. | Conversion |
| Sel. | Selectivity |
| By-Prod | Heavy By-Products |
| Res Time | Residence Time |

TABLE 9

Ionic Liquid Catalyst

| Res Time (s) | Bz Conv. (wt %) | EtBz Sel. (%) | EtBz Yield (%) | DEB Sel. (%) | By-Prod Sel. (%) |
|---|---|---|---|---|---|
| 300 | 14.84 | 80.18 | 11.89 | 11.92 | 7.90 |
| 600 | 20.75 | 77.07 | 15.99 | 14.41 | 8.52 |
| 900 | 26.05 | 73.82 | 19.23 | 16.33 | 9.85 |
| 1800 | 33.30 | 66.88 | 22.27 | 18.30 | 14.82 |
| 3600 | 38.42 | 63.48 | 24.39 | 20.32 | 16.20 |
| 5400 | 40.35 | 62.86 | 25.30 | 20.77 | 16.37 |
| 8100 | 44.33 | 57.72 | 25.56 | 20.48 | 22.00 |
| 10800 | 44.8 | 57.13 | 25.56 | 20.91 | 21.96 |

TABLE 10

Red Oil Catalyst

| Res Time (s) | Bz Conv. (wt %) | EtBz Sel. (%) | EtBz Yield (%) | DEB Sel. (%) | By-Prod Sel. (%) |
|---|---|---|---|---|---|
| 180 | 1.50 | 41.42 | 0.62 | 8.62 | 49.96 |
| 360 | 15.45 | 71.72 | 11.08 | 15.06 | 13.22 |
| 600 | 25.78 | 68.20 | 17.58 | 16.61 | 15.19 |
| 960 | 27.74 | 68.15 | 18.91 | 17.09 | 14.76 |
| 1800 | 34.45 | 58.96 | 20.30 | 16.59 | 24.45 |
| 3000 | 35.14 | 61.05 | 21.45 | 17.89 | 21.06 |
| 5700 | 36.62 | 62.46 | 22.87 | 19.30 | 18.24 |
| 9060 | 41.91 | 56.92 | 23.86 | 19.38 | 23.70 |
| 12660 | 43.85 | 53.06 | 23.27 | 18.21 | 28.72 |

We claim:

1. A process for the alkylation of aromatics by reacting an aromatic hydrocarbon with an olefin in the presence of an ionic liquid catalyst composition comprising
    (a) a compound of the formula $R_nMX_{3-n}$ wherein R is a C1–C6 alkyl group, M is aluminum or gallium, X is a halogen atom and n is 0, 1 or 2, and
    (b) at least one compound selected from the group consisting of a hydrocarbyl substituted imidazolium halide, a hydrocarbyl substituted pyridinium halide, and a mixture thereof,
wherein at least one of the hydrocarbyl substituents in the imidazolium halide is an alkyl group having 1–18 carbon atoms.

2. A process according to claim 1 wherein the hydrocarbyl substituted imidazolium halide or a hydrocarbyl substituted pyridinium halide is selected from 1,3-dialkyl imidazolium halides and 1-alkyl pyridinium halides.

3. A process according to claim 2 wherein at least one of the alkyl substituents in the dialkyl imidazolium halide has 5–18 carbon atoms.

4. A process according to claim 1 wherein hydrocarbyl substituted imidazolium or pyridinium halide is selected from the group consisting of:
    1-methyl-3-ethyl imidazolium chloride,
    1-ethyl-3-butyl imidazolium chloride,
    1-methyl-3-butyl imidazolium chloride,
    1-methyl-3-butyl imidazolium bromide,
    1-methyl-3-propyl imidazolium chloride,
    1-methyl-3-hexyl imidazolium chloride,
    1-methyl-3-octyl imidazolium chloride,
    1-methyl-3-decyl imidazolium chloride,
    1-methyl-3-dodecyl imidazolium chloride,
    1-methyl-3-hexadecyl imidazolium chloride,
    1-methyl-3-octadecyl imidazolium chloride,
    1-methyl-3-hexyl-imidazolium chloride,
    1-methyl-3-octyl-imidazolium chloride,
    1-methyl-3-decyl-imidazolium chloride,
    1-methyl-3-dodecyl-imidazolium chloride,
    1-methyl-3-hexadecyl-imidazolium chloride,
    1-methyl-3-octadecyl-imidazolium chloride,
    ethyl pyridinium bromide,
    ethyl pyridinium chloride,
    ethylene pyridinium dibromide,
    ethylene pyridinium dichloride,
    butyl pyridinium chloride and
    benzyl pyridinium bromide.

5. A process according to claim 1 wherein the ionic liquid comprises a ternary melt of:
   (a) a compound of the formula $R_nMX_{3-n}$ wherein R is a C1–C6 alkyl radical, M is aluminium or gallium, X is a halogen atom and n is 0, 1 or 2,
   (b) at least one of a hydrocarbyl substituted imidazolium halide and a hydrocarbyl substituted pyridinium halide, and
   (c) at least one of a hydrocarbyl substituted quaternary ammonium and a hydrocarbyl substituted phosphonium halide.

6. A process according to claim 5 wherein component (c) in the ternary melts comprises at least one of tetra-alkyl ammonium halides and tetra-alkyl phosphonium halides in each of which the alkyl group suitably has 1–20, preferably 1–18 and more preferably from 1–6 carbon atoms.

7. A process according to claims 5 or 6 wherein the relative mole ratios of components (a), (b) and (c) is such that the ratio of component (a):[(b)+(c)] in the ternary melt ionic liquid is in the range from 1:2 to 3.0:1 and the ratios of (b) : (c) in the range from 0.01:1, so that the resultant ionic liquid is a liquid at room temperature.

8. A process according to claim 1 wherein the olefins used for the alkylation reaction are C2–C10 olefins.

9. A process according to claim 1 wherein the aromatic hydrocarbons that can be alkylated are monocyclic, bi-cyclic or poly-cyclic aromatics.

10. A process according to claim 9 wherein the aromatic hydrocarbons being alkylated are selected from benzene, toluene and naphthlenes.

11. A process according to claim 1 wherein the mole ratio of olefin to the aromatic hydrocarbon used for the alkylation reaction is in the range from 0.1 to 0.9.

12. A process according to claim 1 wherein the alkylation reaction is carried out at a temperature in the range from 80 to 200° C. and at a reaction pressure in the range from 0.5 to 3.0 MPa.

13. A process according to claim 1 wherein the alkylation reaction is carried out in an atmosphere inert under the reaction conditions.

14. A process according to claim 1 wherein the ionic liquid is used in an amount from 0.1 to 1.0% w/w based on the total weight of the hydrocarbon reactants in the reaction mixture to catalyse the alkylation reaction.

15. A process according to claim 1 wherein the ionic liquid is supplemented by an alkyl halide co catalyst.

16. A process according to claim 15 wherein the alkyl halide is ethyl chloride and tertiary butyl chloride.

* * * * *

UNITED STATES PATENT AND TRADEMARK OFFICE
CERTIFICATE OF CORRECTION

PATENT NO. : 5,994,602
DATED : November 30, 1999
INVENTOR(S) : ALA'A K. ABDUL-SADA et al.

It is certified that error appears in the above-identified patent and that said Letters Patent is hereby corrected as shown below:

Title page, [22] should read --Filed: July 29, 1997--.

Title page, [86], insert as the second line:
    --PCT Filed: Feb. 9, 1995--.

Title page, [63] should read --Continuation of application Ser. No. 08/513,810, filed Sep. 5, 1995, abandoned.--

Title page, [30], change "9402569" to --9402569.9--.

Column 9, line 49, "[Et$_4$N]/" should be --[Et$_4$N]Cl/--; line 57, "$^1$NMR" should be --$^1$H NMR--; line 66, "Stendard" should be --Standard--; "&" (first occurrence) should be --of--.

Column 10, lines 3 and 20, "$^1$NMR" should read --$^1$H NMR--.

Signed and Sealed this

Twenty-fifth Day of July, 2000

Attest:

Q. TODD DICKINSON

Attesting Officer

Director of Patents and Trademarks